(12) United States Patent
Rucker, Jr.

(10) Patent No.: US 6,772,761 B1
(45) Date of Patent: Aug. 10, 2004

(54) GAS DELIVERY TUBE

(76) Inventor: Joseph W. Rucker, Jr., 3221 Stein Blvd., Eau Claire, WI (US) 54701

( * ) Notice: Subject to any disclaimer, the term of this patent is extended or adjusted under 35 U.S.C. 154(b) by 0 days.

(21) Appl. No.: 10/224,060

(22) Filed: Aug. 19, 2002

(51) Int. Cl.[7] ............................................. A61M 16/00
(52) U.S. Cl. ............. 128/207.14; 128/128; 128/207.18
(58) Field of Search ....................... 128/200.24, 200.26, 128/201.26, 202.27, 207.14, 207.15, 207.16, 207.18, 911, 912, DIG. 26; 604/101.01, 101.04, 39, 43, 523, 524, 526, 527, 93.01, 94.01, 95.03; 600/432–435

(56) References Cited

U.S. PATENT DOCUMENTS

| | | | | |
|---|---|---|---|---|
| 3,964,488 A | * | 6/1976 | Ring et al. ............. | 128/207.14 |
| 4,278,082 A | | 7/1981 | Blackmer | |
| 4,363,323 A | * | 12/1982 | Geiss ......................... | 604/281 |
| 4,753,233 A | | 6/1988 | Grimes | |
| 5,333,608 A | * | 8/1994 | Cummins .............. | 128/207.14 |
| 5,509,408 A | * | 4/1996 | Kurtis ................... | 128/207.14 |
| 5,546,936 A | * | 8/1996 | Virag et al. ............ | 128/207.14 |
| 5,794,619 A | | 8/1998 | Edelman et al. | |
| 5,800,414 A | * | 9/1998 | Cazal ......................... | 604/280 |
| 5,827,242 A | * | 10/1998 | Follmer et al. ............. | 604/282 |
| 6,001,079 A | * | 12/1999 | Pourchez ..................... | 604/43 |
| 6,419,660 B1 | * | 7/2002 | Russo ........................ | 604/180 |
| 6,443,156 B1 | * | 9/2002 | Niklason et al. ........ | 128/207.14 |
| 6,463,927 B1 | * | 10/2002 | Pagan ................... | 128/200.26 |
| 6,513,527 B1 | * | 2/2003 | Abdel-Aziz ............ | 128/207.14 |
| 6,582,536 B2 | * | 6/2003 | Shimada ..................... | 148/519 |

* cited by examiner

*Primary Examiner*—Henry Bennett
*Assistant Examiner*—Teena Mitchell
(74) *Attorney, Agent, or Firm*—Anthony Bourget

(57) ABSTRACT

A gas delivery tube includes a flexible tube having a tube wall, a first end for connecting to a supply of gas, and a second end having an orifice insert portion for insertion into the orifice of a patient, and forming means contained within the tube wall for selectively forming the tube to the face and into the orifice of a patient, the forming means extending into the orifice insert portion, whereby the tube may be formed to the face of a patient and into the orifice of the patient in a variety of configurations.

27 Claims, 9 Drawing Sheets

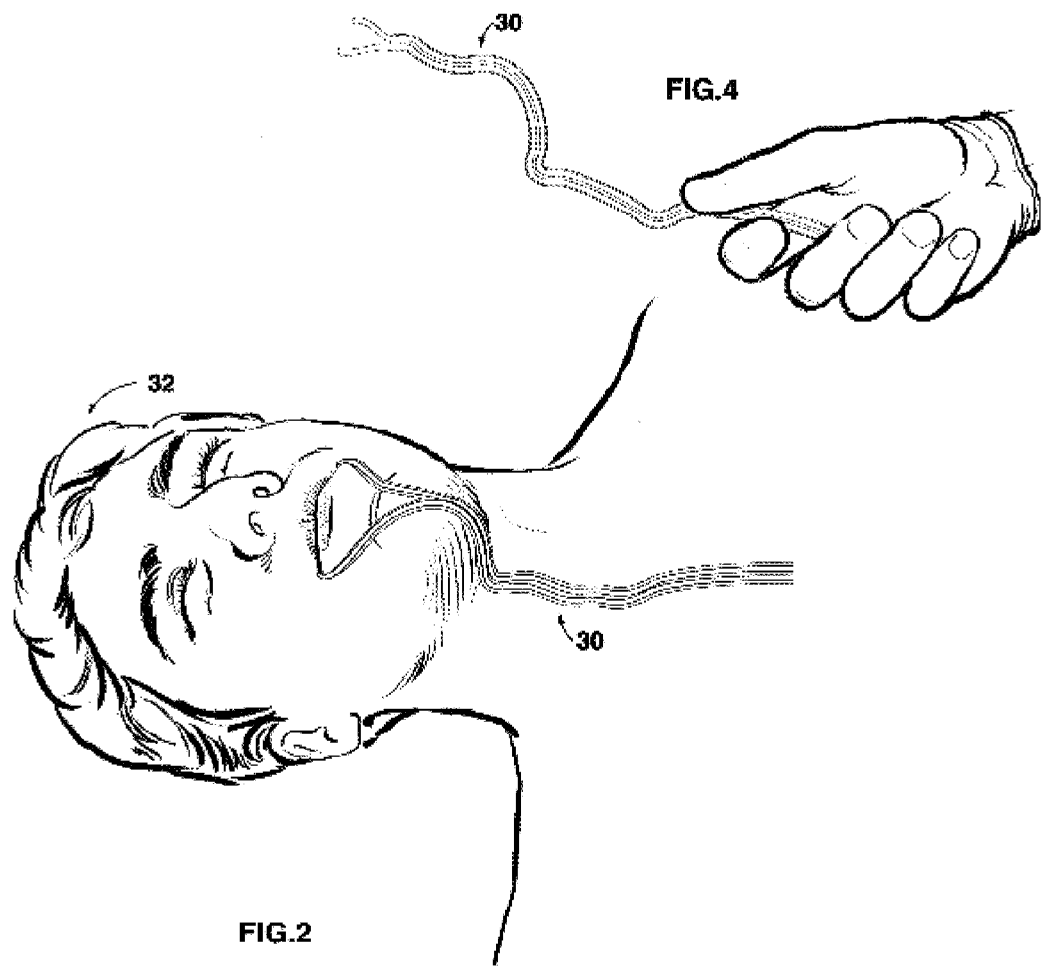
FIG.4
FIG.2
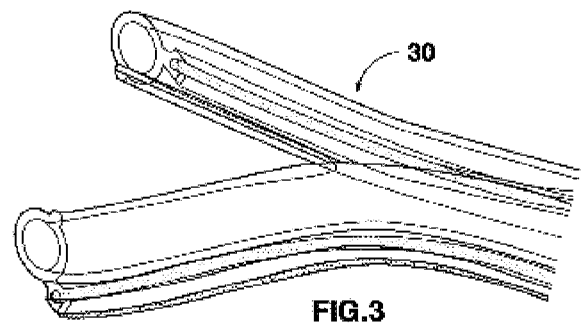
FIG.3

GAS DELIVERY TUBE

FIELD OF THE INVENTION

This invention relates to gas delivery tubing, and more particularly to a delivery tube used for supplying gas such as oxygen to the nose or mouth of a patient.

DESCRIPTION—BACKGROUND OF PRIOR ART

Gas delivery tubes, sometimes referred to as nasal cannulas, are useful in a variety of types of surgery and for therapeutic and other health care purposes. The cannula is often inserted into the patient's nostrils. Eliminating or reducing the discomfort of the gas-supplying tubes has been a focus of various patents. Some of those patents, to name a few, include U.S. Pat. No. 4,753,233 issued to Jerry L. Grimes on Jun. 28, 1988, U.S. Pat. No. 4,278,082 issued to Richard H. Blackmer on Jul. 14, 1981, U.S. Pat. No. 5,794,619 issued to Robert Edelman, et al on Aug. 18, 1998.

There are a variety of surgical procedures which require the delivery of gas, such as oxygen, to a patient. When a surgeon operates on or about the head of a patient, the delivery of gas can become more complicated. Many common devices for delivery include a cannula with delivery tubes that either loop over the ears of a patient, or which are held in place by a friction fit in many instances. Having the tubing extend from the ears of the patient often limits the working space for a surgeon. In the case of facial surgery, it is preferred that the gas tubes not inhibit the surgeon's movements, and that they are sufficiently removed from the surgical area so that the surgeon can operate freely, or with little intrusion. In many cases standard tubing gets in the way of operating procedures, thus tending to cause delay or other nuisance which would preferably be avoided. Limiting the tubing to nasal contact is also limiting, especially where surgery is required to a patient's nose, upper lip, or surrounding area. Further, it is important to have comfortable post-surgical positioning of gas tubing so as not to cause discomfort to the patient's affected facial area, yet it is also important to maintain a sufficient gas delivery tubing configuration.

Applicant has originated a practice of inserting a paper clip into the open end of a standard flexible plastic tube for the delivery of nasal gas. The paper clip assists with selective positioning and re-positioning of the tube about a patient's face. Applicant and others have found such paperclip technique and configuration to work reasonably well; however, it lacks many features useful to the surgeon or patient. Particularly, the paperclip is constantly exposed to the gas within the otherwise sterile tube. The paperclip may also tend to clog or reduce the volume of gas flow since it occupies a position within the hollow tube. Insertion and positioning of the clip can also be awkward and sometimes difficult, and set-up of the paperclip requires further attention in case materials are not readily available or where cutting of the tube or clip is required. The paperclip also extends a relatively short distance within the tube, thus limiting the range of selective positioning or contouring about a patient's face. The paperclip can also be displaced from the tube, resulting in loss of function and also exposing a hazardous pointed tip.

Previous approaches to sufficiently deliver gas have made great focus on patient comfort, however, such approaches have not sufficiently addressed surgeon functionality or patient comfort of facially affected areas.

Therefore, it is an object of the present invention to provide a gas delivery tube that may be aligned to the face of the user in a variety of configurations and contours.

It is another object of the present invention to provide a gas delivery tube which will maintain proper alignment and fit as desired by a surgeon or practitioner.

It is still another object of the present invention to provide a gas delivery tube which can be selectively configured so as to not interfere with the working of a surgeon or other practitioner.

It is another object of the present invention to provide a gas delivery tube which provides great comfort to a patient while insuring sterile delivery of gas to the patient.

The features, benefits and objects of the invention will become apparent to those skilled in the art by reference to the following description, claims and drawings.

BRIEF SUMMARY OF THE INVENTION

The present invention is directed to a soft flexible delivery tube for delivering gas to a patient. The present invention also includes a method of use of the flexible delivery tube.

In one embodiment of the invention, the soft flexible delivery tube includes a flexible tube having a tube wall, a first end for connecting to a supply of gas, and a second end having a orifice insert portion for insertion into a selected orifice of a patient. A forming means is also contained within the tube wall for selectively forming the tube to the face of a patient and into the orifice of a patient. The tube may then be formed to the face of the patient and into the selected orifice of the patient in a variety of configurations. In a further aspect of the embodiment, the forming means extends into the orifice insert portion.

In another embodiment of the invention, a delivery tubing for delivering gas to the patient includes at least two flexible tubes. Each of the tubes comprise a gas source end for connecting to a gas source, and an orifice end having a flexible orifice insert portion for insertion into a selected orifice of the patient. Independent forming means are coupled with the flexible tube for forming the tube to the face and into the orifice of the patient independent of any other forming means of the at least two flexible tubes. Connecting means is included for connecting together the at least two flexible tubes. Each of the flexible tubes of the delivery tubing may be independently formed to the face of a patient and into an orifice of the patient in a variety of configurations. A further aspect of the delivery tubing includes forming means which extends into the orifice insert portion, and where the connecting means extends substantially the length of the at least two tubes.

In another embodiment of the invention, the gas delivery tube comprises a flexible tube having a tube wall, a first end for connecting to a supply of gas, and a second end having an orifice insert portion for insertion into the orifice of a patient. A formable wire is contained within a foot integrally connected to the tube wall for selectively forming the tube to the face and into the orifice of a user. The tube may be formed to the face of a patient and into the orifice of the patient in a variety of configurations.

In another embodiment of the invention, the flexible delivery tubing for delivering gas to a patient includes at least two flexible independently adjustable tubes, each of the tubes comprising a first gas source end for connecting to a gas source, and a second orifice end having a flexible orifice insert portion for insertion into a selected orifice of the patient, and a formable wire contained within the tube and extending substantially a length of the tube. A bridge connecting the flexible tubes is included, the bridge running substantially the length of the tubes. The flexible delivery tubing may be flexibly positioned relative to the patient, and each of the flexible tubes of the delivery tubing may be independently formed to the face of a patient and into a selected orifice of the patient in a variety of configurations.

A further embodiment of the invention includes the method corresponding to the above. The flexibility and forming features of the present invention adds to the versatility of use by surgeons and to the comfort of patients.

BRIEF DESCRIPTION OF THE DRAWINGS

FIG. 2 is a perspective view of the nasal gas delivery tubing of the present invention as placed on a patient's face extending from a chin location.

FIG. 3 includes a partial close-up view of the delivery tubing as shown in FIG. 2.

FIG. 4 is a perspective view of the delivery tubing as shown in FIG. 2.

DETAILED DESCRIPTION OF THE PREFERRED EMBODIMENTS

Figure 1:
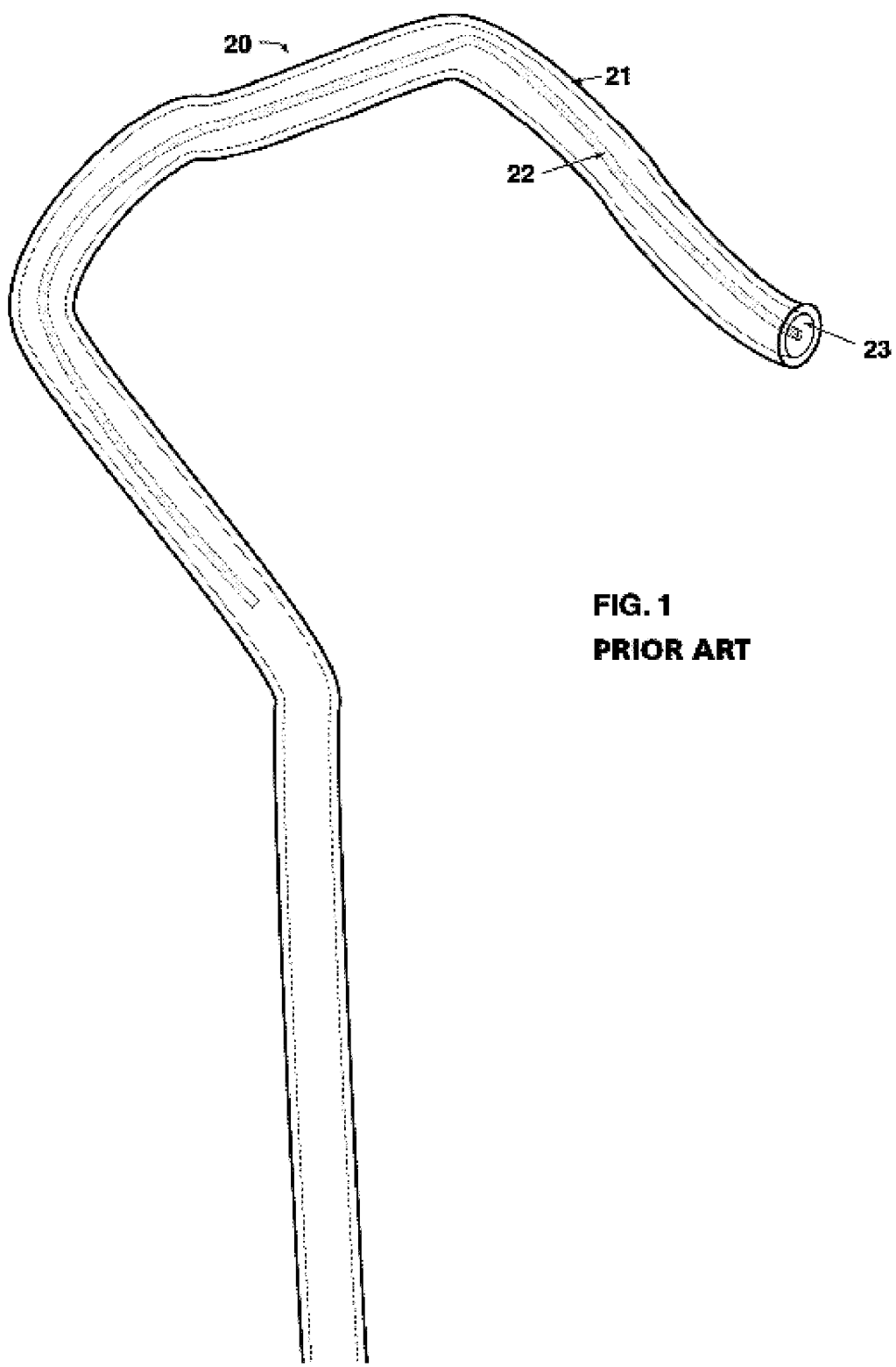
FIG. 1 is a perspective view of a prior art delivery tube containing a paper clip.
Figure 5:
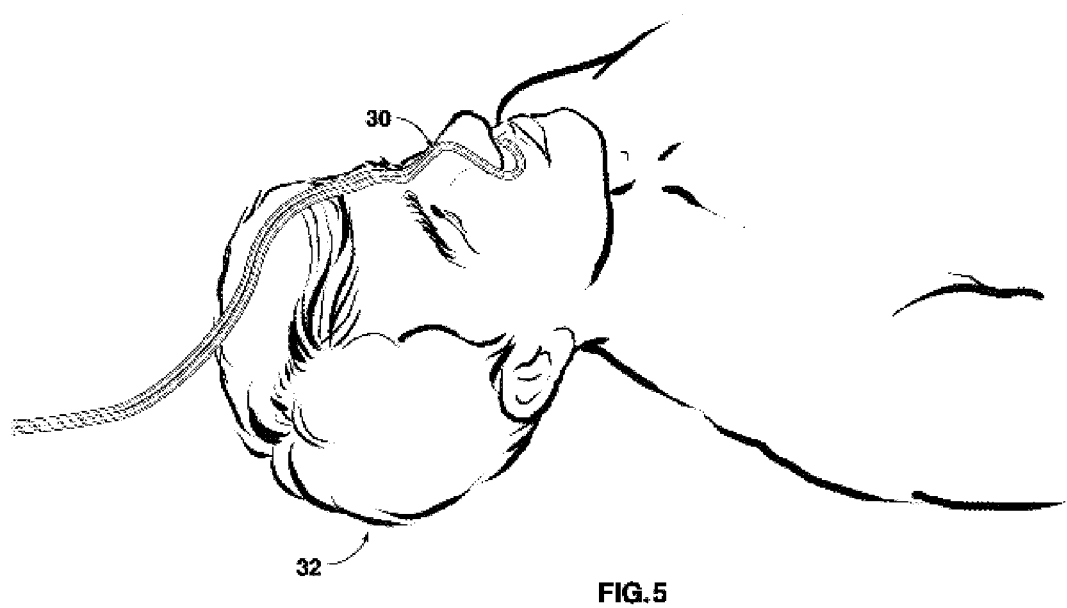
FIG. 5 is a perspective view of the delivery tube of the present invention as positioned from the forehead of a patient.

FIG. 1 represents a prior art cannula 20 used for supplying gas to a patient. Cannula 20 includes hose 21 and paperclip 22 which is bent into a desired shape so that hose 21 can be inserted into the nostril of a patient. A recognized problem with the prior art cannula 20 is exposure of the paperclip 22 within the sterile hose 20. Other drawbacks of the cannula include reduction of the volume of gas flow since the paperclip is included within the hollow channel 23. The paperclip is also limited in its length and is awkward and sometimes difficult to insert. It is also subject to dislodging or extension from within the channel, resulting in a hazard to the patient and surgeon.

In referring to the remaining drawings wherein like numerals represent like parts throughout the several views, FIGS. 2, 5, 10, and 11 represent a gas delivery tubing 30 of the present invention positioned in various configurations on a patient 32. It can be appreciated that the tubing can accommodate a variety of configurations, only some of which are shown in the drawings. For instance, the tubing may run across one or both cheeks, over or around either eye, along the jaw-line, from the temple area, etc, and may lay straight or wind in a curved path, all while matching the contour of the face. Removal of tubing 30 from the face of the patient as shown in FIG. 4 illustrates the forming feature of tubing 30 in which the facial contour is maintained. The variety of configurations allows for a surgeon to select the most appropriate positioning for the task at hand, which may often include facial surgery. Positioning of the tubing 30 away from the surgical area is desired for several reasons. Moreover, the tubing can be conveniently re-positioned and set into a new configuration as surgery progresses. Tubing 30 may extend to the nostrils or the mouth of a patient, either alternatively or simultaneously. When referring to an orifice of a patient herein, such reference is directed to either the mouth and/or nostril of a patient, or both.

Figure 6:
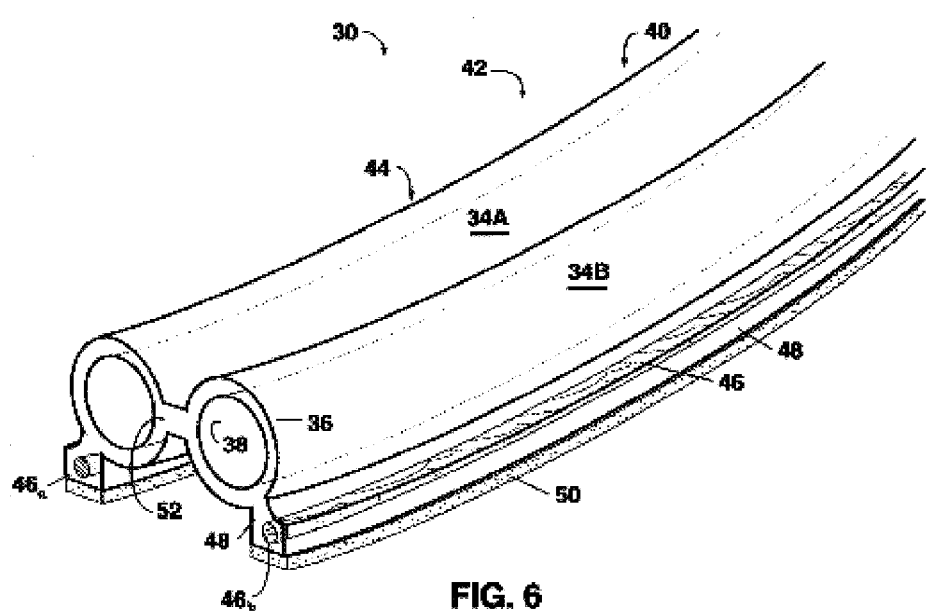
FIG. 6 is a perspective view of the delivery tubing of the present invention.

As shown in FIG. 6, tubing 30 comprises tube 34a and tube 34b. Each of the tubes 34 are similar, and reference to one is meant to include reference to the other. Tube 34 includes a tube wall 36 defining bore 38 which runs the length of tube 34. A first end 40 is provided for connecting to a gas source or a tube or connector running to a gas source (gas source not shown). Second end 42 includes an insert portion 44 for insertion into an orifice of a patient 32. Independent forming means 46 is coupled with tube 34. As shown in FIG. 6, forming means 46 extends into insert portion 44. Preferably, forming means 46 extends to the end of insert portion 44. Forming means 46 preferably extends substantially the length of at least one of the tubes 34a and 34b. Additionally, forming means 46 is preferably enclosed as shown so as not to minimize exposure to the atmosphere or the gas.

Figure 7:
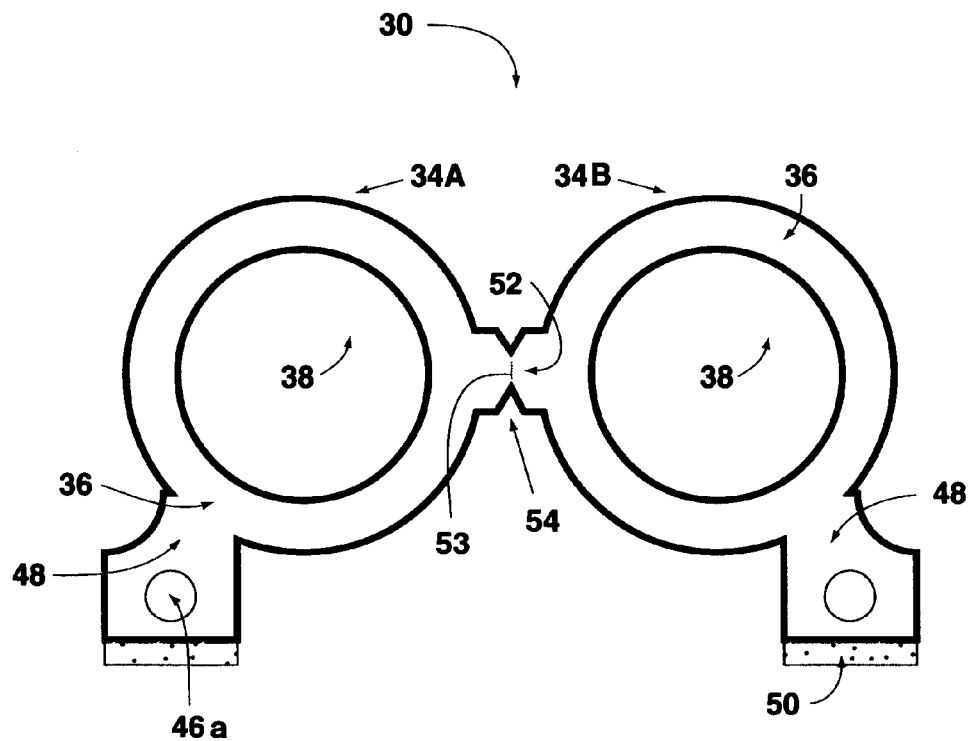
FIG. 7 is an end view of the tubing in FIG. 6.

In one aspect of the present invention, as shown in FIGS. 6 and 7, forming means 46 is contained within foot 48 and may run the entire length of tube 34a. Foot 48 is integrally connected to tube wall 36. Adherent means 50 is coupled to foot 48 so tube 34 may be adhered to the face of a patient. Adherent means 50 may include an adhesive which is exposed after removal of a peel-strip (no shown). Greater adherence of tubing 30 is achieved where each tube 34a and 34b includes adherent means 50. Foot 48 provides a foundation in which forming means 46 may be coupled and also provides a greater surface area for adherent means 50 to be in contact with a patient 32.

Figure 8:
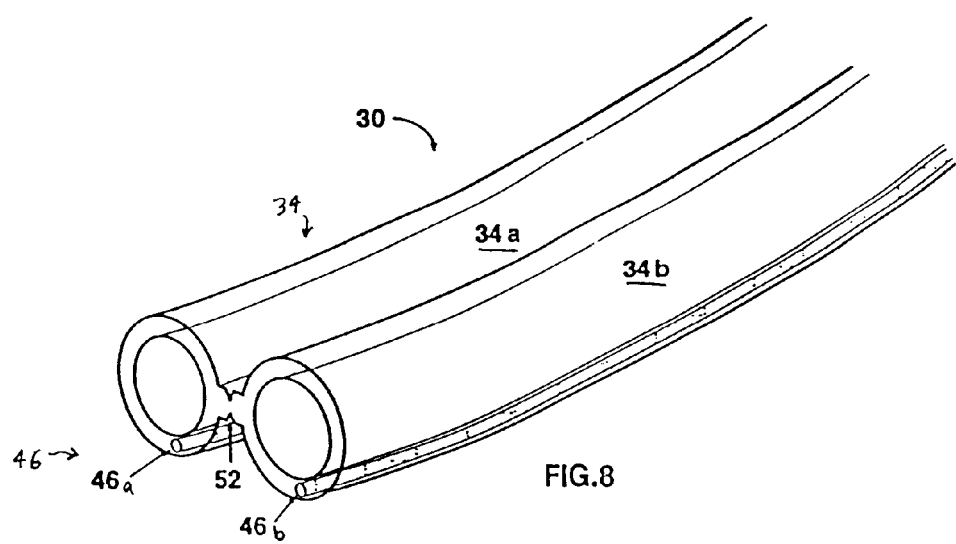
FIG. 8 is a perspective view of a further aspect of the delivery tubing of the present invention.

An alternative aspect of the present invention is shown in FIG. 8, where forming means 46 is contained within tube wall 36. Forming means 46 includes means for selectively forming tube 34 to the face and to (and/or into) the nostril or mouth of a patient. Forming means 46 allows the tube 34 to be selectively deformed into a variety of configurations. Forming means 46 preferably includes a formable wire, such as stainless steel, or other material having similar properties such that such material can be bent and re-bent into a desired position. Such material preferably is pliable and retains its desired shape when manipulated. Independent forming means 46 is independent in that it allows for forming or contouring of the tube 34 without assistance or association with any other forming means that may be included with another tube 34. For instance, forming means 46a contained in tube 34a is independent and does not utilize the forming means 46b contained in tube 34b. While tubes 34a and 34b may connect with bridge 52, forming means 46a is not contacted to or connected with forming means 46b. Forming means 46a is independent of forming means 46b. When connecting means 52 is split or selectively separated, each tube 34a and 34b may be independently formed into desired position utilizing independent forming means 46a and 46b, respectively.

Figure 9:
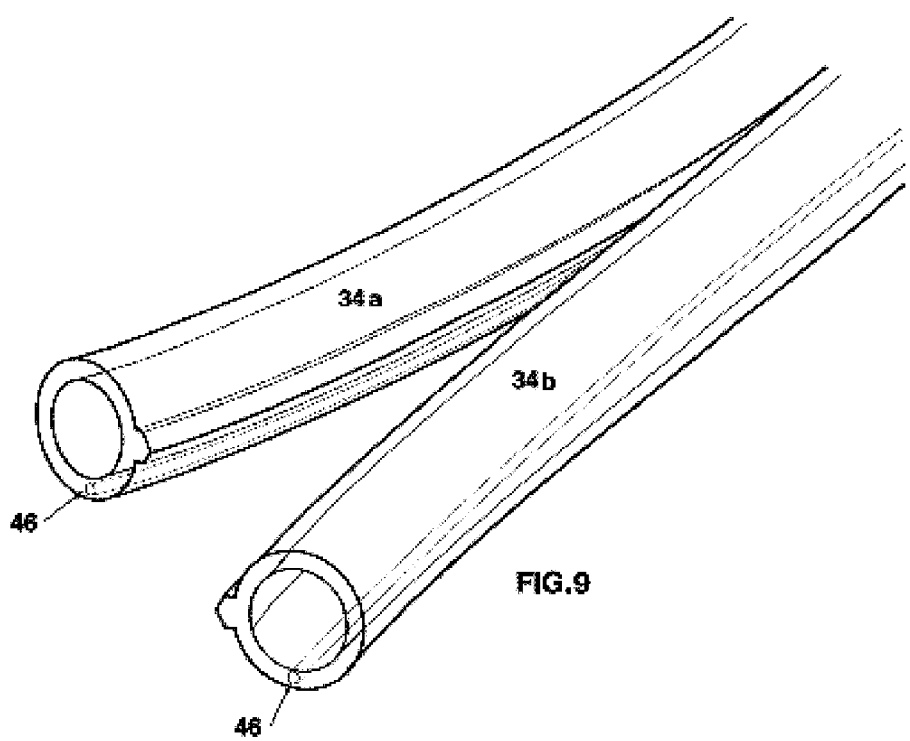
FIG. 9 is a perspective view of the split delivery tubing shown in FIG. 8.
Figure 10:
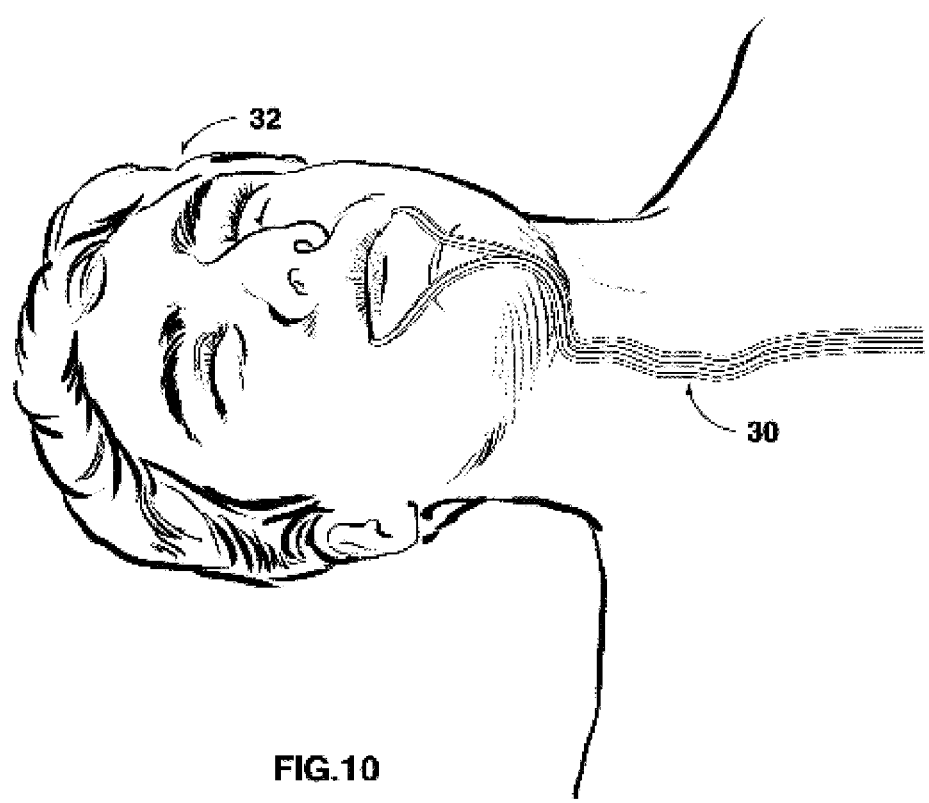
FIG. 10 is a perspective view of the delivery tubing of the present invention as alternatively placed about a patient's face.
Figure 11:
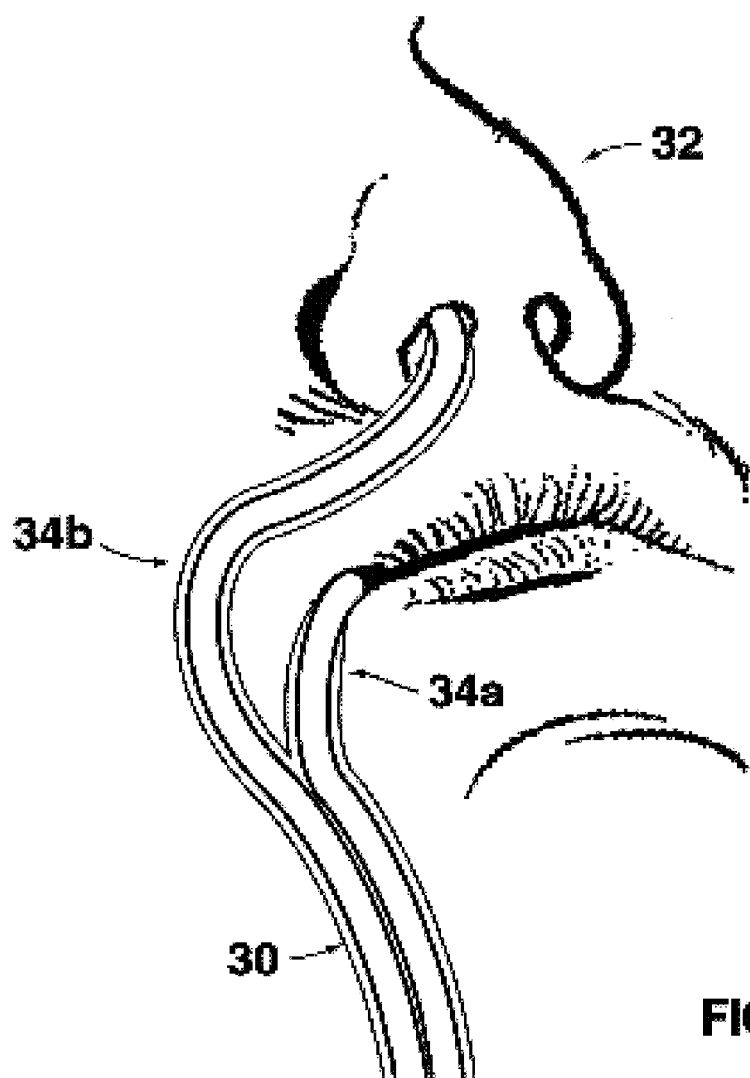
FIG. 11 is a perspective view of the delivery tubing of the present invention as alternatively place about a patient's face.

As shown in FIGS. 3 and 9, tubing 30 may be split to have selective separation between tubes 34a and 34b. Tubing 30 includes connecting means 52 which includes a bridge 52 coupling tube 34a with tube 34b. Connecting means 52 may include bridge 52 which is integrally connected between tubes 34 such that connecting means is longitudinally connected. Bridge 52 may be made of the same flexible tubing material as tubes 34, and may be integrally connected to tubes 34. A user may separate tubes 34 by pulling apart the ends of each tube 34 such that bridge 52 tears. Bridge 52 extends the length of the tubes 34. As shown in FIGS. 2, 10, and 11, however, it can be appreciated that bridge 52 need only extend substantially the length of the tubes 34, since the tubes 34 are split to accommodate use. Bridge 52 preferably includes means 53 for selectively separating the tubes 34. Separating means 53 may include perforations, notches 54, openings, grooves, indentations, or gaps or other common separation means to aid separation of the tubes 34. Separating means 53 may extend the length of the tubes 34, and are preferably intermittent perforations. Preferably, separating means is included within the connecting means 52 at least adjacent the orifice insert portion 44. Thus, splitting of the tubes 34 is easily accommodated for convenient positioning of the split tubes 34 near the desired orifices of a patient. Preferably bridge 52 has a thickness such that it may be torn without resulting in a tear of tube walls 36. A user splits tubing 30 so that a desired orifice or orifices receive a separate tube 34. The tubes may also be inserted into the patient's mouth, or one into the patient's mouth and the other into the nostril. A surgeon may designate one tube 34a as an oxygen supply and the other tube 34b as a CO2 return. This assists in monitoring gas content. Splitting the tubing 30 also allows each tube 34 to be configured along an independent path across a patient's face to accommodate for complicated facial surgery if required.

A further embodiment of the present invention may be ascertained from the structures shown in FIGS. 3 and 9 where it may be appreciated that the delivery tube of the present invention described above includes a single of the tubes 34a or 34b described above. The forming means 46 extends into the orifice insert portion 44. A further aspect includes use of a foot 48 integrally connected to the tube wall 34 for selectively forming the tube to the face and into the orifice of a patient.

Tubing 30 may be wound into a coil or upon a dispenser. A user may thereby unwind a desired length of tubing to be cut for handy use. As shown in FIG. 4, a length of approximately six to ten inches generally provides sufficient contour length for desired patient use. A singular tube 34a may operate independently of any companion tube 34b.

As shown in FIG. 11, tubing 30 is split to accommodate insertion in different orifices, namely one tube 34a is inserted into the mouth of a patient and the other tube 34b is inserted into one nostril of the patient 32. Tubing 30 is secured onto the patient's face and into each orifice with adherent means 50. Independent forming means 46a and 46b independently form and secure tubes 34a and 34b into position.

A further embodiment of the present invention includes a method of supplying gas to a patient in accordance with the foregoing descriptions, and as provided in the claims.

The descriptions above and the accompanying drawings should be interpreted in the illustrative and not the limited sense. While the invention has been disclosed in connection with the preferred embodiment or embodiments thereof, it should be understood that there may be other embodiments which fall within the scope of the invention as defined by the following claims. Where a claim is expressed as a means or step for performing a specified function it is intended that such claim be construed to cover the corresponding structure, material, or acts described in the specification and equivalents thereof, including both structural equivalents and equivalent structures.

I claim:

1. A face conforming delivery tubing for delivering gas to a patient while accommodating access to selected areas of the patient's head, said tubing comprising:
    at least two flexible tubes, each of said tubes comprising:
        a gas source end for connecting to a gas source, and an orifice end having a flexible orifice insert portion for insertion into a selected orifice of the patient; and
        independent forming means coupled with said flexible tube for forming said tube to the face of the patient and into the orifice of the patient, said forming means extending to an end of said orifice insert portion; and
    connecting means for connecting together said at least two flexible tubes;
    whereby each of said flexible tubes of said delivery tubing may be independently formed to the face of a patient and into an orifice of the patient in a variety of configurations.

2. A delivery tubing according to claim 1 wherein said forming means extends into said orifice insert portion.

3. A delivery tubing according to claim 1 wherein said forming means is contained within a wall of at least one of said at least two flexible tubes.

4. A delivery tubing according to claim 1 wherein said forming means extends substantially a length of at least one of said at least two flexible tubes.

5. A delivery tubing according to claim 1 wherein said forming means includes a formable wire.

6. A delivery tubing according to claim 5 wherein said formable wire comprises stainless steel.

7. A delivery tubing according to claim 1 wherein said connecting means extends substantially the length of said at least two tubes.

8. A delivery tubing according to claim 7 wherein said connecting means is an integral bridge longitudinally connecting said at least two tubes.

9. A delivery tubing according to claim 7 wherein said connecting means includes means for selectively separating said flexible tubes adjacent said orifice end portions.

10. A delivery tubing according to claim 9 wherein said selectively separating means includes one from the group of a perforation, a notch, an opening, a groove, an indentation.

11. A delivery tubing according to claim 1 wherein said delivery tubing includes a foot integrally connected to a wall of at least one of said two flexible tubes, said forming means contained within said foot.

12. A delivery tubing according to claim 1 wherein at least one of said at least two flexible tubes includes adherent means for adhering said tube to the face of a patient.

13. A face conforming delivery tube for delivering gas to a patient while accommodating access to selected areas of the patient's head, said tube comprising:
    a flexible tube having a tube wall, a first end for connecting to a supply of gas, and a second end having an orifice insert portion for insertion into a selected orifice of a patient; and
    forming means contained within said tube wall for selectively forming said tube to the face of a patient and into the orifice of a patient;
    whereby said tube may be formed to the face of a patient and into the selected orifice of the patient in a variety of configurations.

14. A delivery tube according to claim 13 wherein said forming means extends into said orifice insert portion.

15. A delivery tube according to claim 13 wherein said forming means extends to an end of said orifice insert portion.

16. A delivery tube according to claim 13 wherein said delivery tube includes a foot integrally connected to said tube wall, said forming means contained within said foot.

17. A delivery tube according to claim 13 wherein said forming means includes a formable wire.

18. A delivery tube according to claim 17 wherein said formable wire comprises stainless steel.

19. A delivery tube according to claim 13 wherein said delivery tube includes adherent means for adhering said tube to the face of a patient.

20. A face conforming gas delivery tube for delivering gas to a patient while accommodating access to selected areas of the patient's head comprising:
   a flexible tube having a tube wall, a first end for connecting to a supply of gas, and a second end having an orifice insert portion for insertion into the orifice of a patient; and
   a formable wire contained within a foot integrally connected to said tube wall for selectively forming said tube to the face and into the orifice of a patient;
   whereby said tube may be formed to the face of a patient and into the orifice of the patient in a variety of configurations.

21. A delivery tube according to claim 20 wherein said formable wire extends into said orifice insert portion.

22. A delivery tube according to claim 20 wherein said delivery tube includes adherent means for adhering said tube to the face of the patient.

23. A face conforming flexible delivery tubing for delivering gas to a patient while accommodating access to selected areas of the patient's head, said tubing comprising:
   least two flexible, independently adjustable tubes, each of said tubes comprising:
      a first gas source end for connecting to a gas source, and a second orifice end having a flexible orifice insert portion for insertion into a selected orifice of the patient; and
      a selectively formable face conforming and orifice insertable wire contained within said tube and extending substantially a length of said tube; and
   a bridge connecting said flexible tubes, said bridge running substantially the length of said tubes;
   whereby said flexible delivery tubing may be flexibly positioned relative the patient and each of said flexible tubes of said delivery tubing may be independently formed to the face of a patient and into a selected orifice of the patient in a variety of configurations.

24. A delivery tubing according to claim 23 wherein said formable wire extends into said orifice insert portion.

25. A delivery tubing according to claim 23 wherein said bridge integrally and longitudinally connects said tubes.

26. A delivery tubing according to claim 23 wherein said tubing includes a foot integrally connected to a wall of at least one of said two tubes, said formable wire contained within said foot.

27. A method of supplying gas to an orifice of a patient, said method comprising the steps of:
   providing delivery tubing comprising:
      at least two flexible tubes, each of said tubes comprising:
         a first gas source end for connecting to a gas source, a second orifice end having a flexible orifice insert portion for insertion into a selected orifice of the patient; and
         independent forming means coupled with said flexible tube for forming said tube to the face of the patient and into the orifice of the patient; and
         connecting means for connecting together said at least two flexible tubes;
      attaching said orifice insert portion to a selected orifice of the patient;
      attaching said first gas source to the gas source; and
      administering gas to the patient;
   whereby each of said flexible tubes of said delivery tubing may be independently formed to the face of the patient and into an orifice of the patient in a variety of configurations.

* * * * *